US00PP35181P2

(12) United States Plant Patent
Hansen

(10) Patent No.: US PP35,181 P2
(45) Date of Patent: May 23, 2023

(54) ***HIBISCUS* PLANT NAMED 'LILAC CRUSH'**

(50) Latin Name: ***Hibiscus* hybrid (L.)**
Varietal Denomination: Lilac Crush

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,784

(22) Filed: Nov. 22, 2022

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./226, 257
See application file for complete search history.

*Primary Examiner* — Karen M Redden

(57) ABSTRACT

A new and distinct cultivar of winter-hardy, herbaceous, perennial, hybrid *Hibiscus* plant named 'Lilac Crush' comprising flattened, rounded, compact, mound habit of multiple, well-branched, mostly upright stems producing flowers from the bottom to the top of the plant for at least eight weeks beginning mid-summer. Flowers have large petals of deep-lilac with a small, dark-red, shiny eye surrounded by a narrow rose-red zone and a large column displaying light yellow-colored pollen nearly the entire length. The foliage is primarily tri-lobed with medium to dark-green color.

2 Drawing Sheets

Botanical classification: *Hibiscus* hybrid (L.).
Variety denomination: 'Lilac Crush'.

STATEMENT REGARDING PRIOR DISCLOSURES UNDER 37 CFR 1.77(b)(6)

The first publically released non-enabling description was a photograph and brief description of the new plant first on Dec. 1, 2021, when it was listed on websites operated by Walters Gardens, Inc. and Proven Winners®, followed on Jun. 8, 2022, as a photograph and brief description in the "Walters Gardens 2022-2023 Catalog, followed with a non-enabling description and photograph in the "Walters Gardens, Inc. 2022-2023 Catalog on Jun. 8, 2022. Walters Gardens, Inc and Proven Winners® obtained the new plant and all information about the new plant from the inventor. The first disclosure, in the form of a sale, was made by Walters Gardens, Inc. on Feb. 28, 2022, to The Big Greenhouse, Ltd. followed by sales to Midwest Groundcovers, LLC., Bordine Nursery, Four Star Proven Winners® and Quality Greenhouses by Walters Gardens, Inc. Walters Gardens, Inc. obtained the new plant and all information relating thereto, from the inventor. No plants of *Hibiscus* 'Lilac Crush' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Lilac Crush' hybridized under the direction of the inventor on Sep. 6, 2018, at a wholesale perennial nursery in Zeeland, Mich. The new plant is a hybrid of the complex, unreleased, proprietary hybrid known as 17-x-1 (not patented) times the unreleased, proprietary hybrid 16-62-9 (not patented). Into the trial process, the new plant was assigned the breeder code labeled 18-253-1. Both parents have a complex mixture of species in them, comprising the species: *moscheutos, lasiocarpus*, and *coccineus*.

*Hibiscus* 'Lilac Crush' was first asexually propagated in the late summer of 2020 by sterile shoot-tip tissue culture and later by shoot-tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'Lilac Crush' differs from its parents as well as all other hardy herbaceous *Hibiscus* known to the applicant in many traits. The most similar *Hibiscus* known to the applicant are: 'Berrylicious' U.S. Plant Pat. No. 24,062, 'Berry Awesome' U.S. Plant Pat. No. 27,936, 'Fantasia' U.S. Plant Pat. No. 11,853, 'Plum Crazy' U.S. Plant Pat. No. 11,854, and 'Plum Fantasy' U.S. Plant Pat. No. 25,986.

'Berrylicious' has flowers of mauve-lavender, a smaller habit. 'Berry Awesome' has a slightly smaller habit, the flowers are deeper lavender-pink with greater folding and the foliage has a greater burgundy coloration. 'Fantasia' has smaller habit with less branching and the flowers are a more reddish lavender. 'Plum Crazy' has a slightly smaller habit, the foliage more burgundy coloration and the flower is more reddish plum. 'Plum Fantasy' has a taller and narrower habit, the foliage is more burgundy blushed, and the flowers are more puckered and have a more reddish-magenta color.

The female parent was not retained as either a plant or with photography, so no comparison is possible. The male parent has a shorter more open habit, mostly tri-lobed foliage and the flower is smaller, more cupped, and has a deeper red center eye and the base color is lavender.

*Hibiscus* 'Lilac Crush' is a unique hardy herbaceous *Hibiscus* with the following combined traits:

1. Winter-hardy compact perennial with flattened, rounded, mound habit of multiple, well-branched, basal stems.
2. Many flat rotate flowers are produced from the bottom to the top of the plant.
3. Flowers produced for at least eight weeks beginning mid-summer.
4. Flower petals of deep-lilac with a small, dark-red, shiny eye, surrounded by a narrow rose-red zone.
5. Flower a large column with anthers nearly the entire length and light-yellow pollen.
6. Foliage is mainly tri-lobed with a medium dark-green color.

BRIEF DESCRIPTION OF THE DRAWINGS

The photographs of the new plant demonstrate the overall appearance of the plant, including the unique traits grown in Zeeland, Mich. The colors are as accurate as reasonably possible with color reproductions. Ambient light spectrum, source, and direction may cause the appearance of minor variations in color.

DETAILED BOTANICAL DESCRIPTION

Figure 1:
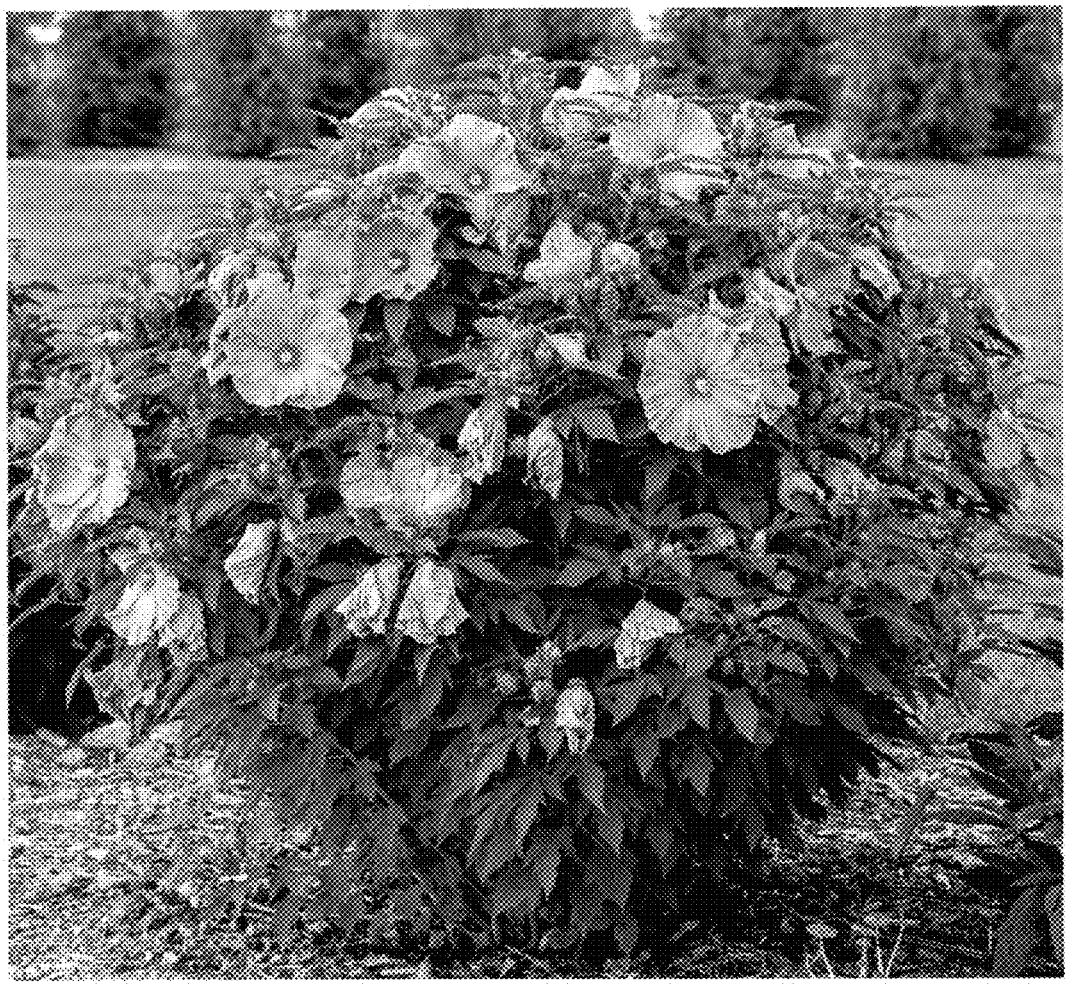
FIG. 1 shows a three-year-old plant in full flower in a display garden.
Figure 2:
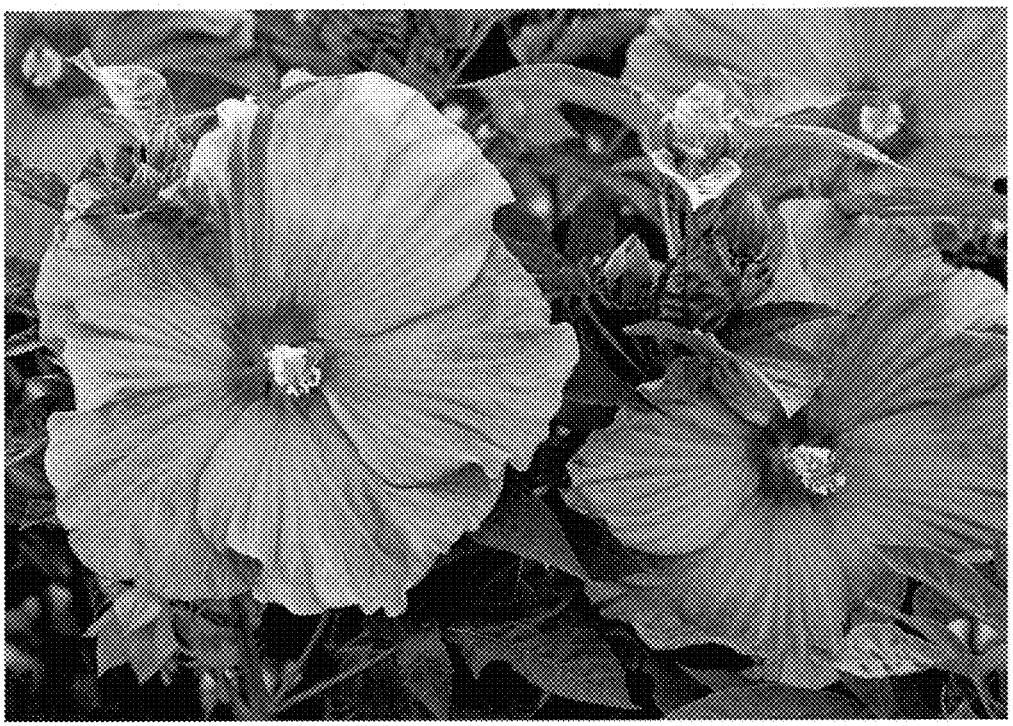
FIG. 2 shows a close-up of the flower.

The following descriptions and color references are based on the 2015 edition of The Royal Horticultural Society Colour Chart except where common dictionary terms are used. The new plant, *Hibiscus* 'Lilac Crush', has not been observed under all possible environments. The phenotype may vary slightly with different environmental conditions, such as temperature, light, fertility, moisture, and maturity levels, but without any change in the genotype. The following observations and size descriptions are of three-year-old plants in the loamy-sand full-sun trial garden at a nursery in Zeeland, Mich. with supplemental fertilizer and water as needed. The plants are of natural habit and were not treated with plant growth regulators, nor were they pinched at any time in the growth year.

Parentage: The female or seed parent is known by the breeder code 17-x-1, the male or pollen parent is known by the breeder code 16-62-1;

Propagation:

*Method*.—Shoot tip cuttings and sterile shoot-tip plant tissue culture.

*Time to initiate roots from tissue culture*.—About two weeks.

*Rooting habit*.—Normal, branching, developing thick to about 2.5 cm diameter, fleshy; root color creamy yellow nearest RHS 161D depending on soil type.

*Crop time*.—Under normal summer growing conditions 12 to 16 weeks to flower in a four-liter container from cutting; plant vigor very good.

Plant description:

*Plant habit*.—Winter-hardy herbaceous perennial with about 54 thick, mostly upright, heavily-branched stems producing an upright spreading mound to about 148 cm tall and about 240 cm wide.

*Stem*.—Cylindrical, glabrous, glaucous; to about 148 cm tall and about 22 mm diameter at base, average about 141 cm tall and about 12 mm diameter at base.

*Stem color*.—Between RHS 146D and RHS 145A.

*Lateral branches*.—Up to 7 per stem, average about 5 per stem; cylindrical, glabrous, glaucous; to about 20 mm long and 2 mm diameter at base, not branched distally.

*Lateral branch color*.—Between RHS 146D and RHS 145A.

*Internode color*.—Indistinguishable in color from surrounding stem.

Foliage description: Mostly tri-lobed, rarely 5-lobed; lobes dissected nearly to petiole, leaves in proximal one-third of stems dissected to about half or one-third of the way to petiole; alternate; apex narrowly acute; base rounded to nearly cordate; margin coarsely and irregularly dentate; glabrous abaxial and adaxial; adaxial and abaxial surface matte when mature, adaxial lustrous when first expanding; leaf blades to about 14.8 cm long and about 15.8 cm across, average blade size 12.0 cm long and 12.5 cm wide; no fragrance detected.

*Foliage color*.—Young expanding leaves adaxial between RES 146B and RHS 146C, abaxial nearest RHS 148B without obvious anthocyanin blushing; mature leaves adaxial between RHS 137A and RHS 137B with very light anthocyanin blushing, abaxial between RHS 147B and RHS 147C with very light anthocyanin blushing.

*Veins*.—Palmate; lustrous and flat on adaxial; matte and costate on abaxial.

*Vein color*.—Young adaxial midrib and veins nearest RHS 147C, abaxial veins between RHS 147C and RHS 146C with midrib nearest RHS 147C; mature adaxial midrib nearest RHS 195B distally and proximally nearest RHS 182D with secondary veins variable nearest 146D, abaxial midrib and proximal secondary veins nearest RHS 145C and distal secondary veins nearest RHS 146B.

*Petioles*.—Mostly cylindrical and slightly applanate on whole adaxial side; glaucous; glabrous; to about 11 cm long and 4.5 mm diameter at base, average size about 8.5 cm long and 3 mm wide at base.

*Petiole color*.—Ventral between RHS 145A and RHS 145B, dorsal proximally between RHS 145A and RHS 145B faintly blushed anthocyanin, distally nearest RHS 146B with faint blushing nearest 187B.

Flower description: Complete; perfect; actinomorphic; rotate; mostly outward facing; rotate; lasting up to two days on plant; to about 19.5 cm across and cupped to 7.0 cm deep, with column extending 40.0 mm long; flower size decreasing distally;

Buds one day prior to anthesis: Ellipsoidal with bluntly rounded apex with petals slightly opened and bluntly rounded base; sepals adpressed to petals; about 6.2 cm long and about 3.8 cm diameter in middle;

Bud color one day prior to anthesis: Exposed petal color nearest RHS N77B and calyx nearest RHS 146D;

Epicalyx: Typically, 11 to 13 per flower; linear; entire, glabrous, with margin micro ciliate; dull surface abaxial and adaxial; narrowly acute apex and truncate base, distally arcuate around calyx; about 20.0 mm long and about 2.5 mm wide at base;

Epicalyx color: Adaxial nearest RHS 146C and abaxial nearest RHS 146B without anthocyanin blushing;

Calyx: Star-shaped hypanthium; campanulate; 20 mm deep and 52 mm across;

Sepals: Five, fused in basal 12 mm and free in distal 22 mm; acute apex; glabrous; margin entire, edentate; abaxial and adaxial surfaces matte; individually about 34 mm long when flattened, about 17 mm wide at fusion;

Sepal color: Adaxial between RHS 146D and RHS 145A, veins nearest RHS 146B; abaxial between RHS 146C and RHS 146D without anthocyanin blushing;

Flowers: Solitary, up to 24 per main stem without pinching; slightly cupped face; mostly outwardly facing; natural spread to about 19.5 cm across and 7 cm deep from stigma to base of calyx; smaller in later season;

Flower lastingness: Persist for one to two days; effective at least eight weeks beginning late July;

Flower fragrance: None detectable;

Petals: Five; glabrous; lustrous eye adaxial and abaxial; adnate to the androecium to form a column, imbricate to about 30% overlapping at widest part (petals overlapping 30% to the petals on either side); palmately veined, primary veins impressed on adaxial and slightly costate abaxial; surface slightly dimpled and slightly puckered longitudinally; rounded with distinct claw and limb; margins entire, edentate; apex rounded; base short claw-like;

Petal size: Average about 12 cm across and about 11 cm long narrowing to claw base about 7 mm across (smaller in later part of flowering season);

Petal color: Adaxial central and distal region nearest RHS 75A where covered by other petal, and between RHS 76B and RHS 76C where exposed to direct sunlight, center eye 5 mm wide nearest RHS 53A, with a more distal eye ring about 12 mm thick nearest RHS 59A; primary veins nearest RHS N77C and secondary veins nearest RHS 76D; abaxial basal 2 mm of eye nearest RHS NN155D, distal 15 mm of eye blend between RHS 67C and RHS 67B, distal blade where adaxial surface covered by another petal nearest RHS 75A, and between RHS 76B and RHS 76C where adaxial surface exposed to sunlight, with primary and secondary veins nearest RHS 76D;

Flower lastingness: One to two days;

Gynoecium: Single; partially enclosed in column;

*Column*.—Glabrous and lustrous; fringed distally with acute apices; about 37 mm long and about 9 mm across at base; with pistil exserted about 11 mm.

*Column color*.—Basal 5 mm nearest RHS 53A and next proximal 5 mm nearest RHS NN155D with some thin longitudinal lines of nearest RHS 53A, distal 20 mm between RHS 53D and RHS NN155D.

*Style*.—Micro-puberulent in region exserted above column, glabrous in region contained in column; about 4.7 cm long, basally penta-furcate in about distal 8 mm; branch diameter about 1.2 mm; color basally nearest RHS NN155C, distally transitioning to between RHS 61C and RHS 61B in exserted portion.

*Stigma*.—Typically, five; flattened ellipsoidal, puberulent, to about 3 mm in diameter and 1 mm tall; color nearest RHS 61A.

*Ovary*.—Superior, conical, rounded to broadly acute apex and flat truncate base; irregularly and longitudinally fluted; about 8 mm across at base and about 8 mm tall; color nearest RHS 145C.

Androecium: Filaments: numerous, about 120; about 4 mm long and about 0.2 mm diameter; attached along the entire length of column; color in proximal portion of column nearest RHS NN155C and distally between RHS 55B and RHS 60D;

*Anthers*.—Flattened reniform; dorsifixed; about 2 mm long and 1 mm across and thick; color nearest RHS 11B; nearest RHS 16C.

Pedicel: Cylindrical; glabrous, mostly straight, glaucous; upright, diameter; decreasing in distal flowers;

Pedicel color: Between RHS 146D and RHS 146C, without anthocyanin;

Peduncle: Cylindrical, glabrous, glaucous; to about 148 cm long and 22 mm diameter at base, average 140 cm long and 12 mm diameter at base; flowering in the distal one-third; with up to seven non-flowering branches that are up to 2 cm long;

Peduncle color: Between RHS 146D and RHS 145A;

Fruit: Penta-loculicidal capsule; puberulent outer surface and pubescent along inner septa with hairs of nearest RHS 158A to about 3 mm long; globose to ellipsoidal, cuspidate apex and truncate base; about 33 mm long and 226 mm diameter; color nearest RHS 200B when mature; about 45 to 90 seeds per fruit;

Seed: Minutely puberulent; globose; about 3 mm in diameter; color nearest RHS N199B;

Resistance: *Hibiscus* 'Lilac Crush' has not displayed any pest and disease resistance beyond that typical of hardy perennial *Hibiscus*.

Growth requirements: The plant grows best with plenty of moisture.

Hardiness at least from USDA zone 4 through 9.

I claim:

1. A new cultivar of hardy herbaceous perennial *Hibiscus* hybrid plant named 'Lilac Crush' as herein illustrated and described.

* * * * *